(12) United States Patent
Toth

(10) Patent No.: US 8,301,230 B2
(45) Date of Patent: Oct. 30, 2012

(54) METHOD FOR REDUCING BASELINE DRIFT IN A BIOLOGICAL SIGNAL

(75) Inventor: Michael S. Toth, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 1070 days.

(21) Appl. No.: 12/284,932

(22) Filed: Sep. 25, 2008

(65) Prior Publication Data

US 2010/0076329 A1    Mar. 25, 2010

(51) Int. Cl.
*A61B 5/0428* (2006.01)

(52) U.S. Cl. .......................................... 600/509; 607/18

(58) Field of Classification Search .................. 600/509; 607/18

See application file for complete search history.

(56) References Cited

U.S. PATENT DOCUMENTS

| | | | |
|---|---|---|---|
| 5,704,365 A * | 1/1998 | Albrecht et al. | 600/515 |
| 5,713,367 A * | 2/1998 | Arnold et al. | 600/517 |
| 6,470,320 B1 | 10/2002 | Hildebrand et al. | |
| 6,533,724 B2 | 3/2003 | McNair | |
| 2002/0099686 A1 | 7/2002 | Schwartz et al. | |
| 2003/0101076 A1 | 5/2003 | Zaleski | |
| 2004/0015337 A1 | 1/2004 | Thomas et al. | |
| 2004/0078232 A1 | 4/2004 | Troiani | |
| 2004/0103001 A1 | 5/2004 | Mazar et al. | |
| 2004/0236188 A1 | 11/2004 | Hutchinson et al. | |
| 2005/0119534 A1 | 6/2005 | Trost et al. | |
| 2006/0025931 A1 | 2/2006 | Rosen et al. | |
| 2006/0173663 A1 | 8/2006 | Langheier et al. | |
| 2006/0224416 A1 | 10/2006 | Lloyd et al. | |

OTHER PUBLICATIONS

K. Kaczmarek et al., "Baseline reduction in two dimensional gel electrophoresis images", ACTA Chromatographica, 2005, 15: pp. 82-96.*

J. Kolibal et al, "MALDI-TOF baseline drift removal using stochastic Berstein approximation", J. Appl. Signal Proc. 2006, 63582: pp. 1-9.*

Y. Sun et al. "ECG signal conditioning by morphological filtering", Computers in Biology and Medicine, 2002, 32(6): pp. 465-479.*

* cited by examiner

*Primary Examiner* — Tammie K Heller
(74) *Attorney, Agent, or Firm* — Willard Jones, II

(57) ABSTRACT

A computer-based method for reducing or eliminating baseline drift from a biological (bio) signal includes the steps of dividing the bio signal into a plurality of shorter signals having fixed time intervals, fitting a corresponding portion of a baseline function to a baseline of a respective one of each of the shorter signals, and subtracting the baseline function from the bio signal, resulting in a bio signal with a flat baseline.

27 Claims, 8 Drawing Sheets

METHOD FOR REDUCING BASELINE DRIFT IN A BIOLOGICAL SIGNAL

BACKGROUND OF THE INVENTION

This invention relates to a method, a system and a device for processing electrocardiac signals, or other biological (bio) signals, to reduce or eliminate baseline drift.

An electrocardiogram (ECG or EKG), is a graphic produced by an electrocardiograph, which records the electrical activity (a signal) of the heart over time. Electrical waves cause the heart muscle to pump. These waves pass through the body and can be measured at electrodes (electrical contacts) attached to the skin. Electrodes on different sides of the heart measure the activity of different parts of the heart muscle. An EKG displays the voltage (a signal) between pairs of these electrodes, and the muscle activity that they measure, from different directions. This display indicates the overall rhythm of the heart, and weaknesses in different parts of the heart muscle. It is a way to measure and diagnose abnormal rhythms of the heart, particularly abnormal rhythms caused by damage to the conductive tissue that carries electrical signals, or abnormal rhythms caused by levels of salts, such as potassium, that are too high or low.

The ability to analyze an EKG signal and detect variances therein, allows for monitoring the physiological condition of a heart. For instance, accurate detection of variances in an EKG signal allows for the detection of heart events, such as heartbeat detection, arrhythmias, ischemias, and a myriad of other events. To detect variances in the EKG signal, it is necessary to minimize or eliminate noise, which also causes variances in an EKG signal, but does not correspond to a physiological event of the heart. Otherwise, the noise variance may be misconstrued as a heart event. In turn, this can lead to a potential misdiagnosis, false positive, missed event, or failure to detect other rhythms, among other undesirable results.

Baseline drift is a type of noise that causes signals, such as an EKG signal, to wander, i.e., drift in a linear or nonlinear fashion. Baseline drift may arise from any number of factors including, but not limited to, drift in electronic signal conditioning, thermal or mechanical stresses at the electrodes, and changes in operation condition, e.g., variations in ambient or body temperature, patient movement, etc.

Present techniques used to minimize baseline drift involve the use of filters. For example, one known method of removing baseline drift involves the use of a high-pass filter to filter out frequencies below a selected cutoff frequency. High pass filters, however, deviate from their ideal models, resulting in undesirable performance. In particular, high pass filters feature "roll-off", which refers to imperfections in the signal response of a digital filter around a cut-off value.

Digital filters attempt to approximate the desired ideal response by increasing the length (order) of their impulse response. Because the digital filters must be causal, delay of the output is a necessary result. The main tradeoffs in digital filters include additional delay and increased numeric precision required as the order of the filter is increased. Therefore, the roll-off is unavoidable as well as a significant delay in the signal when close approximations are required.

FIG. 1 shows a conventional high pass filter response curve 10. An ideal high pass response 5 features a sharp transition from low to high at a cutoff frequency $f_0$. Roll-off is illustrated at a location 12 near the cutoff frequency $f_0$. As shown, the conventional high pass filter allows signals of slightly lower frequency than the cutoff frequency $f_0$ in addition to blocking signals of slightly higher frequency than the cutoff.

FIG. 2 shows a comparison between a conventional high pass response curve 14a and a response curve 14b of a conventional high pass finite impulse response (FIR) digital filter of length 63, in which the filter impulse response has been made longer in an attempt to approximate the ideal response 5. Although the response 14b more closely approximates the ideal response 5 than the response 14a, the response 14b delays the output by a factor of 2. If a lower order filter is needed, it is possible to introduce ripple in the pass band and stop band to increase the slope of the transition region. However, this also introduces other non-ideal response characteristics.

Based on the above descriptions of conventional high pass filters, it can be seen that any realizable high pass filters cannot fully attenuate low frequency noise such as baseline drift in EKG signals (or other bio signals, such as from the brain). The technical problem of baseline drift and other such frequency based noise in a bio signal is potentially extremely serious. This is particularly so when experienced in the field of, for example, EKG signals since errors occurring in readings of an EKG signal can lead to erroneous deductions as to patient condition or required treatments.

BRIEF SUMMARY OF THE INVENTION

According to a first aspect of the present invention, there is provided a computer-based method for reducing baseline drift in a biological (bio) signal, the method comprising: dividing the bio signal into a plurality of shorter signals having fixed time intervals; fitting a corresponding portion of a baseline function to a baseline of a respective one of each of the shorter signals; and subtracting the baseline function from the bio signal, thereby flattening the baseline of the bio signal.

In one embodiment the method is for eliminating baseline drift, resulting in a flat baseline.

According to a second aspect of the present invention, there is provided a device for reducing baseline drift in a biological (bio) signal, the device being constructed and arranged to: divide the bio signal into a plurality of shorter signals having fixed time intervals; fit a corresponding portion of a baseline function to a baseline of a respective one of each of the shorter signals; and subtract the baseline function from the bio signal, thereby flattening the baseline of the bio signal.

Preferably, the device completely eliminates baseline drift, resulting in a flat baseline.

In one embodiment, the device comprises: a communications arrangement configured to receive the bio signal; and a processor to divide the bio signal into a plurality of shorter signals having fixed time intervals, fit a corresponding portion of a baseline function to a baseline of a respective one of each of the shorter signals, and subtract the baseline function from the bio signal, resulting in a bio signal with a flat baseline. In other words, the device includes a processor that is configured to execute the steps on the bio signal so as to produce as a result a bio signal with a flattened baseline.

In one embodiment, the device includes a memory which itself includes instructions configuring the processor to divide the bio signal into a plurality of shorter signals having fixed time intervals, fit a corresponding portion of a baseline function to a baseline of a respective one of each of the shorter signals; and subtract the baseline function from the bio signal, thereby flattening the baseline of the bio signal.

According to a third aspect of the present invention, there is provided a computer-readable storage medium having stored thereon a series of instructions executable by a processor for removing noise from a digital signal, the instructions configured to cause the processor to perform the steps of: dividing the bio signal into a plurality of shorter signals having fixed time intervals; fitting a corresponding portion of a baseline function to a baseline of a respective one of each of the shorter signals; and subtracting the baseline function from the bio signal, thereby flattening the baseline of the bio signal.

DETAILED DESCRIPTION OF THE INVENTION

Exemplary embodiments of the present invention will be described with reference to the removal of low frequency baseline drift from EKG signals. However, it will be appreciated that the exemplary embodiments of the present invention described below may be adapted towards the removal of any type of frequency based noise. Furthermore, the present invention need not be limited to bio signals, but may be applied to any digital signal.

Figure 2:
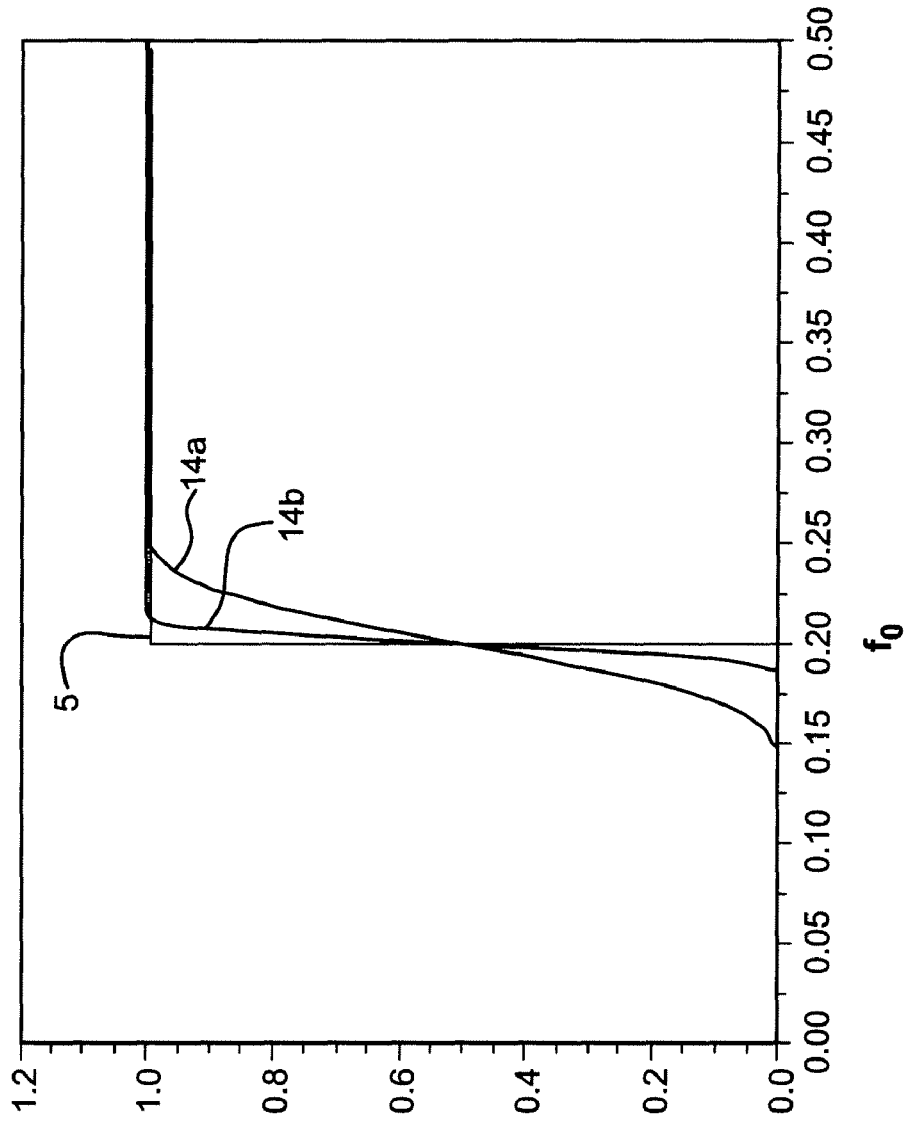
FIG. 2 shows a comparison of two high pass filter responses.
Figure 1:
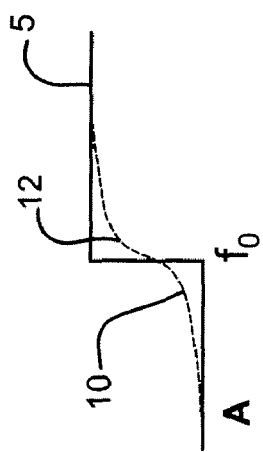
FIG. 1 shows a conventional high pass filter response.
Figure 3:
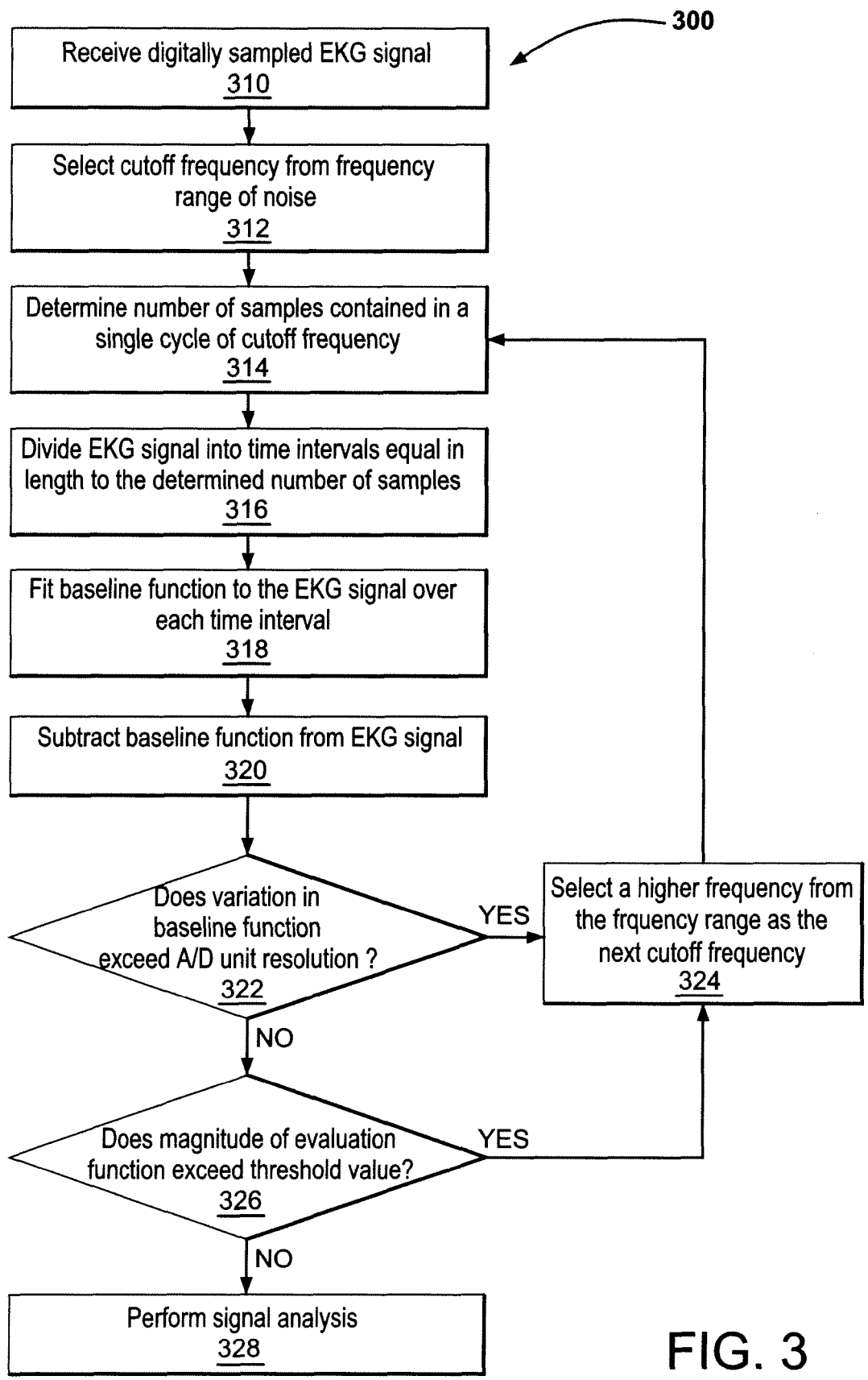
FIG. 3 shows an example of a method for eliminating baseline drift from or at least reducing baseline drift in a bio signal according to an example embodiment of the present invention.

FIG. 3 shows an example of a method 300 for eliminating baseline drift from or at least reducing baseline drift in a bio signal according to an example embodiment of the present invention. The method 300 serves to flatten, i.e. make flatter, and preferably completely flatten, the baseline of a bio signal. The method 300 may be implemented on a computing device with signal processing capabilities. An example of such a computing device will be described below. The method 300 may be implemented in hardware, software or any combination thereof.

In 310, a digitally sampled EKG signal may be received. The digital signal may correspond to an analog EKG signal recorded by a patient monitoring device after the analog signal has been passed through an analog-to-digital (A/D) converter. The digital signal may illustrate one or more heartbeats sensed by an electrode of the monitoring device.

Figure 4:
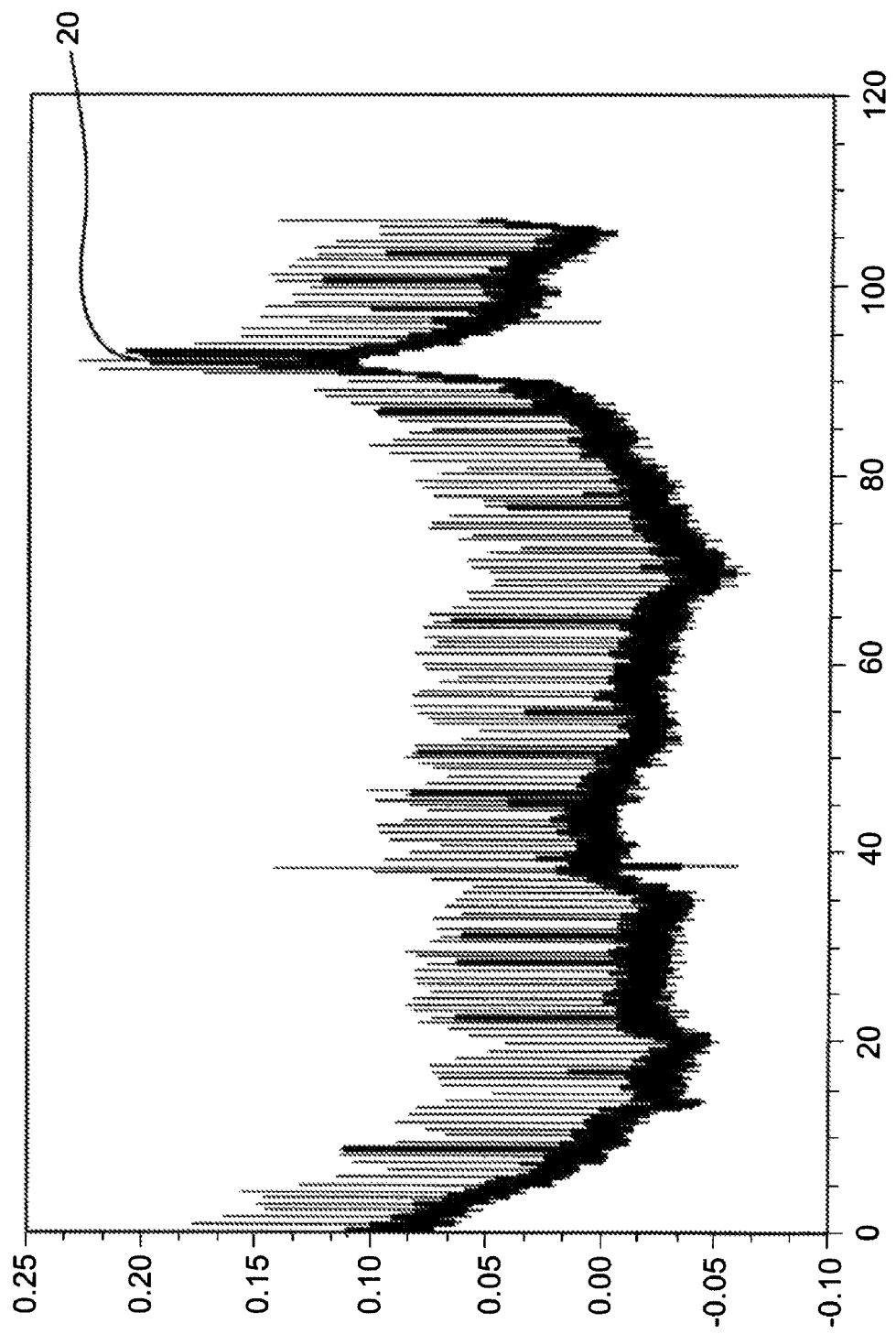
FIG. 4 shows an example of a digitally sampled bio signal.

FIG. 4 shows an example of a digital EKG signal 20. As shown, the signal 20 may be a periodic signal of varying frequency and intensity. The signal 20 is shown plotted as a function of time. The units of the vertical and horizontal axes are microvolts and seconds, respectively. Positive spikes along the signal 20 may correspond to individual heartbeats, e.g., QRS complexes where the peak of each spike may correspond to the R portion of a QRS complex. Computer techniques exist to analyze EKG signals. For example, ecgpuwave is part of the open source PhysioToolkit program and may be used to detect QRS complexes. However, use of programs such as ecgpuwave may not yield accurate or consistent results. This may be especially true if baseline drift is present, as illustrated in FIG. 4. Baseline drift causes the signal 20 to deviate in both the positive and negative directions, e.g., non-linearly. Because the frequency and intensity of the baseline drift can vary, discerning the QRS complexes using analyzing programs such as ecgpuwave may be difficult. It may also be difficult to determine where the QRS complexes are located using the naked eye, since the signal is displayed as a function of time rather than frequency.

Referring back to FIG. 3, in 312 a cutoff frequency may be selected based on a frequency range corresponding to noise. For example, it is known that baseline drift generally varies from 0.5 to 150 Hz. The selection may be performed automatically or user selected. For example, a user may choose to eliminate baseline noise at particular frequencies. Automatic selection may involve selecting the lowest frequency in the range, e.g., 0.5 Hz. The cutoff frequency may be selected so that the cutoff conforms with the Nyquist criteria for a particular frequency in the range. For example, if 0.5 Hz is the particular frequency of interest, the cutoff frequency may be selected to be at least twice that amount, e.g., 1 Hz, in order to avoid aliasing.

In 314, the number of samples contained in a single cycle of the cutoff frequency may be determined. The determination may be performed as a function of a sampling frequency of the digital signal. For example the signal 20 was sampled at a frequency of 1,000 Hz so there are 1,000 samples every second. A cutoff frequency of 1 Hz would, accordingly, correspond to the number of samples contained in one second of data, e.g., 1,000 samples.

In 316, the digital signal may be divided into time intervals equal in length to the determined number of samples. The time intervals may comprise breakpoints for use in fitting a baseline function to the digital signal, as will be described below. If the signal 20 has a length of 100,000 samples, dividing the signal 20 into intervals of 1,000 samples would yield 100 breakpoints. Thus, the location of the breakpoints may be determined as a function of the sampling frequency of the digital signal and the frequencies of interest, e.g., frequencies that correspond to noise.

Figure 5:
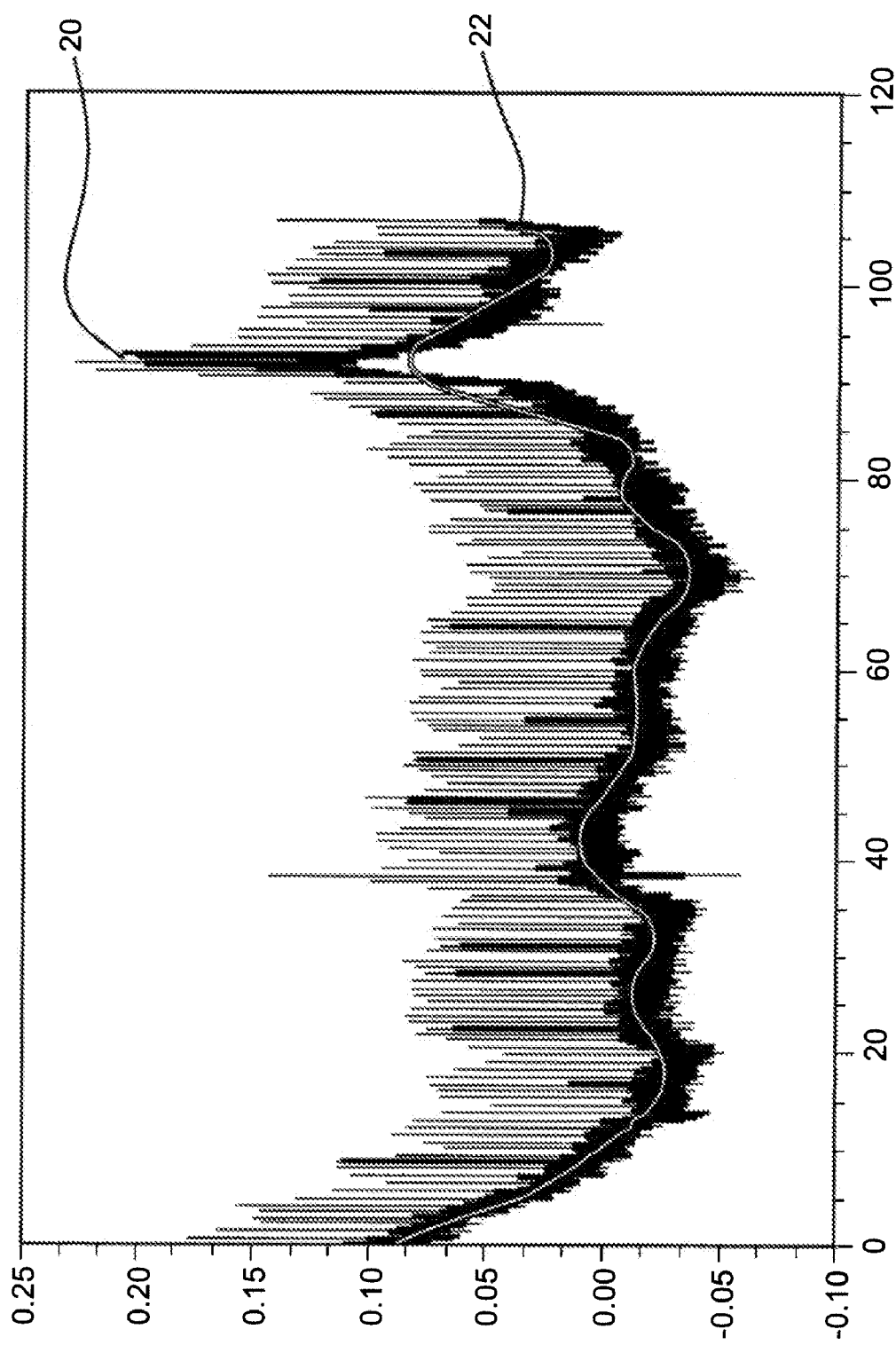
FIG. 5 shows an example of a baseline function fitted to the bio signal of FIG. 4 according to an example embodiment of the present invention.

In 318, the digital signal may be fitted over each time interval to generate a baseline function that spans the entire length of the digital signal. The baseline function may be a piece-wise function comprising a plurality of smaller baseline functions corresponding to each time interval, and formed using cubic-spline interpolation. A cubic polynomial may be generated to fit the digital signal values between each breakpoint, yielding a baseline function that approximates the baseline drift. For each time interval, a cubic function is generated such that it passes through the signal values located at the beginning and end of the time interval, e.g., the breakpoints. FIG. 5 shows an example of a baseline function 22 fitted to the signal 20 using twenty breakpoints. As shown, the baseline function 22 may roughly approximate a low frequency baseline drift in the digital signal 20.

Figure 6:
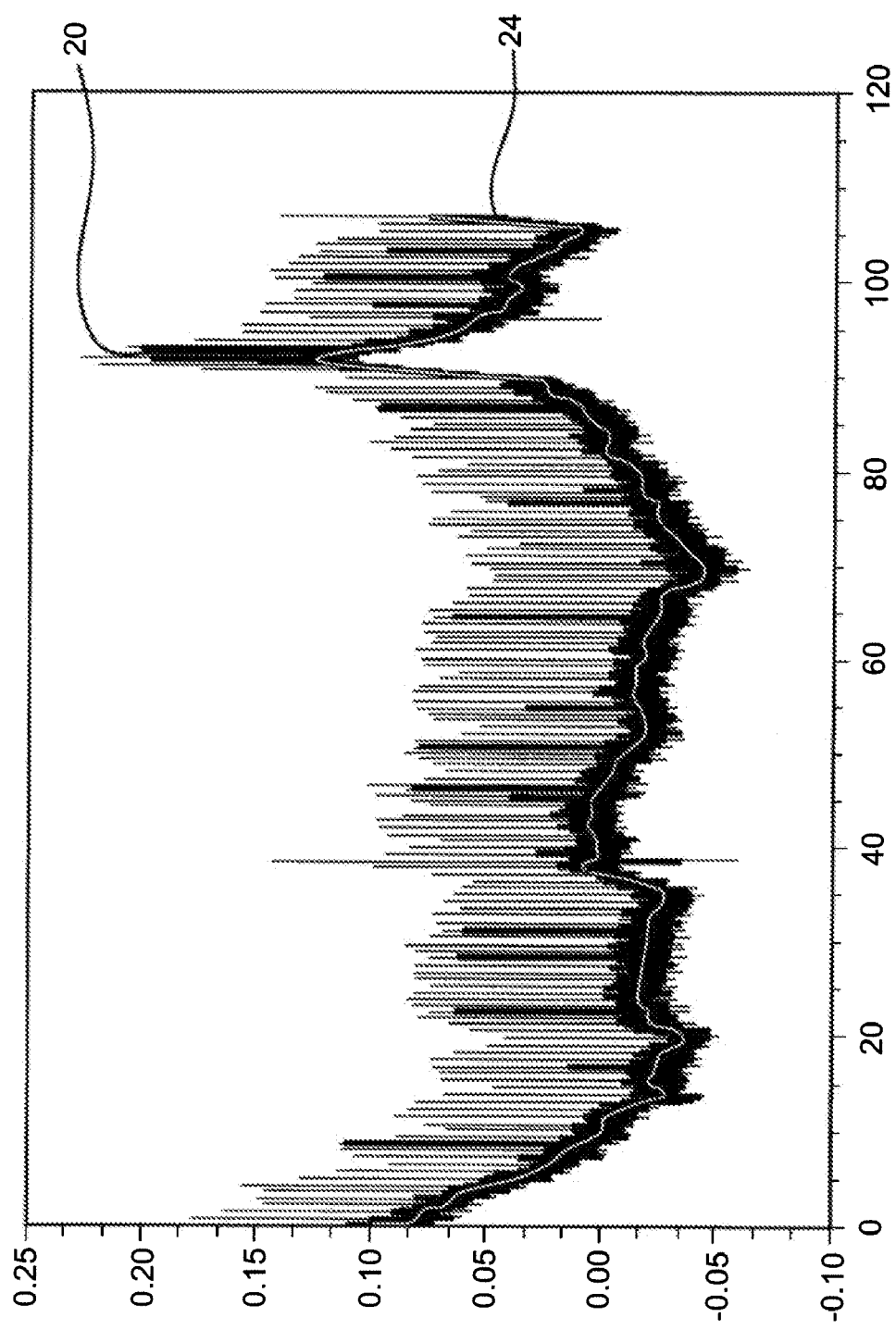
FIG. 6 shows another example of a baseline function fitted to the bio signal of FIG. 4 according to an example embodiment of the present invention.

The exactness of the fit may depend on how many breakpoints are used. Therefore the value of the cutoff frequency selected may influence fit. Generally, the more breakpoints selected (i.e., higher cutoff frequency), the higher the degree of fit. FIG. 6 shows an example of a baseline function 24 fitted to the signal 20 using one hundred breakpoints. Compared to the function 22, the function 24 has a tighter fit which more closely approximates the actual baseline drift. However, it should be noted that selecting too many breakpoints may result in over-fitting. Accordingly, it may be preferable to choose the lowest possible cutoff frequency value which yields an acceptable baseline drift approximation.

Figure 7:
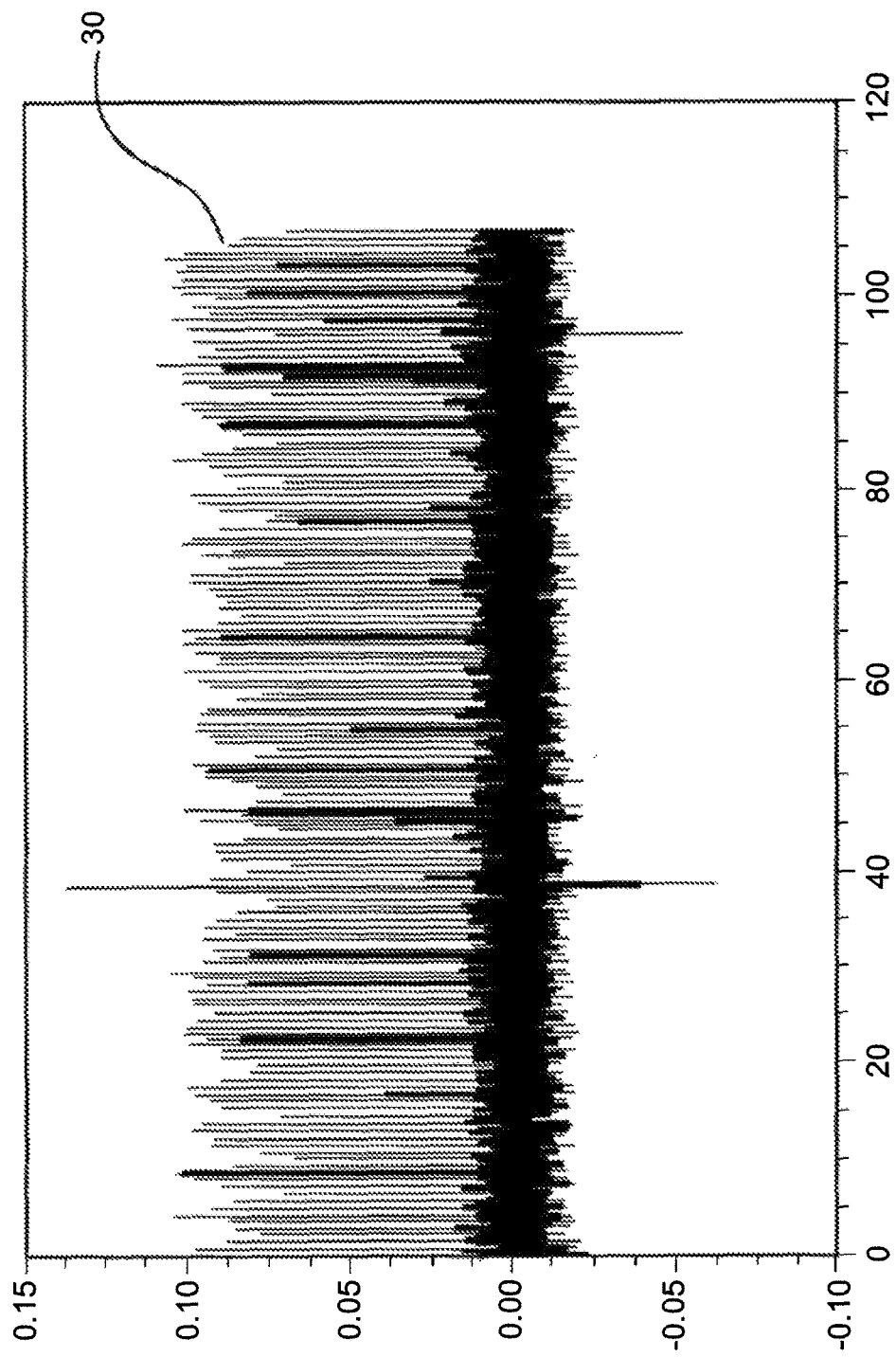
FIG. 7 shows an example of a flat-baselined signal obtained after removing baseline drift from the bio signal of FIG. 4 according to an example embodiment of the present invention.

In 320, the baseline function may be subtracted from the digital signal to generate a flat-baselined EKG signal. Each value in the baseline function may be deducted from a corresponding digital signal value to generate the flat-baselined signal. FIG. 7 shows an example of a flat-baselined signal 30, which is the result of subtracting the signal 24 from the signal 20. As shown, the signal 30 is much flatter compared to the signal 20, allowing for easier signal analysis.

The fitting of the baseline function and the subsequent subtracting of the baseline function from the digital signal may be repeated at different frequencies within the range of frequencies associated with the noise source. Fitting may be repeated based on a determination of whether results of the signal analysis are satisfactory.

One measure of whether the results are satisfactory is to compare the variation in the baseline function to the maximum resolution of a digital representation of the baseline function. The resolution of an A/D converter unit determines the smallest error that can be represented by the A/D unit's output. As an illustrative example, if the gain is 6,400 A/D units per millivolt, then a change in the LSB corresponds to a change of 1/6,400 mV=156 microvolts. If the variation in the baseline function is less than 156 microvolts, then no further improvement may be possible given the A/D resolution. However, if the variation is larger than the magnitude of the LSB change, then the fitting may be repeated, e.g., repeating the cubic-spline interpolation on the new waveform. Each time the fitting is repeated, the variation in the baseline drift may be reduced. In this manner, the fitting may be repeated until the variation is less than or equal to the magnitude of the LSB change. Accordingly, in 322, a determination may be performed whether the variation in the baseline function exceeds the A/D unit's resolution.

If the variation exceeds the A/D unit's resolution, then the method 300 may proceed to 324, where a higher frequency is selected from the frequency range corresponding to the baseline drift. The method 300 then returns to 314.

Figure 8:
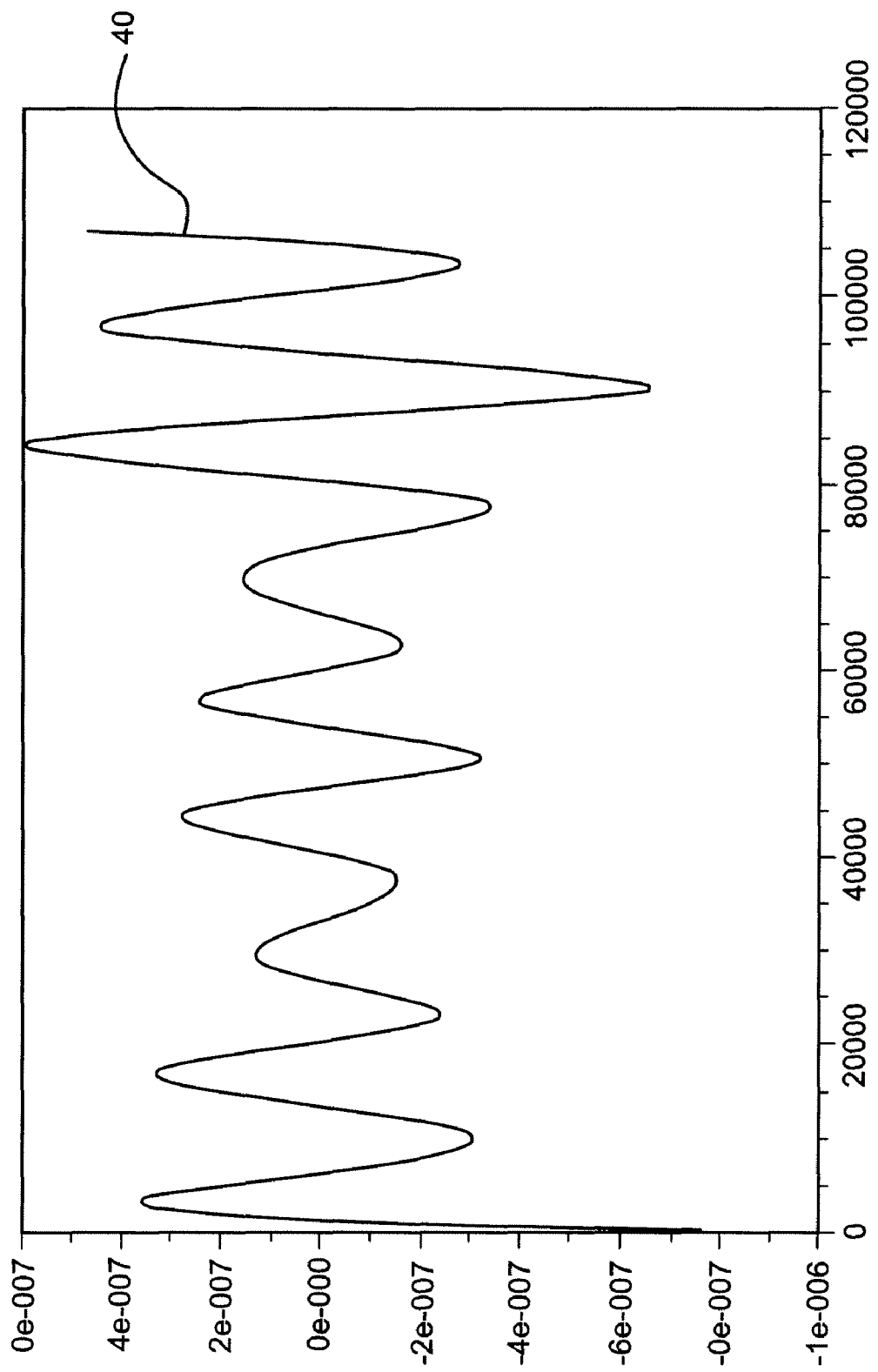
FIG. 8 shows an example of an evaluation function fitted to the flat-baselined signal of FIG. 7.

The fitting may also be repeated based on an evaluation of a flatness of the flat-baselined signal. Flatness may be evaluated by fitting an evaluation function to the flat-baselined signal, e.g., using cubic-spline interpolation or least squares fitting, and viewing the magnitude of the evaluation function. FIG. 8 shows an example of an evaluation function 40 according to an example embodiment of the present invention. The evaluation function 40 may be obtained by applying cubic-spline interpolation to the signal 30. Breakpoints of the evaluation function may be selected to match the locations of each sample in the signal 30. Alternatively, the breakpoints of the evaluation function may be selected to match the breakpoints of the baseline function. Accordingly, if the variation does not exceed the A/D unit's resolution, then the method may proceed to 326, where a determination may be performed whether the magnitude of an evaluation function exceeds a threshold value.

If the magnitude exceeds the threshold value, then the method 300 may proceed to 324 before returning to 314.

If the magnitude does not exceed the threshold value, then the method 300 may proceed to 328, where a signal analysis may be performed on the flat-baselined signal. Clinical points of interest may be determined by, for example, determining the locations of QRS complexes in the flat-baselined signal. The ORS complexes correspond to individual heartbeats and may be found by locating large spikes in the flat-baselined signal, which may be easier to do now that the digital signal has been de-noised. Detection of other points of interest may also be easier using the flat-baselined signal.

Although the method 300 was described with reference to automatic repeated fitting, the repeated fitting may also be performed manually, e.g., by the user manually selecting new cutoff frequencies based on a manual evaluation of flatness. In one embodiment, the user may select random values within the frequency range. In another embodiment, the user may choose to gradually increase the cutoff frequency at each iteration. Cutoff frequency selection may also be selected (either manually or automatically) by, for example, increasing the cutoff frequency by a predetermined amount each time the fitting is repeated (e.g., fixed step or linear increases). In this manner, baseline drift associated with a variety of frequencies may be removed.

It will be also be appreciated that other fitting techniques may be used in addition to cubic-spline interpolation. For example, other types of polynomial interpolation, e.g., quadratic may be used. Polynomial interpolation generally yields a baseline function that passes through each signal value located at the breakpoints. Other fitting techniques may not require such an exact fitting. For example, in another embodiment, a least squares fit may be used to generate a baseline function that approximates the baseline drift without intersecting every signal value at the breakpoints.

Figure 9:
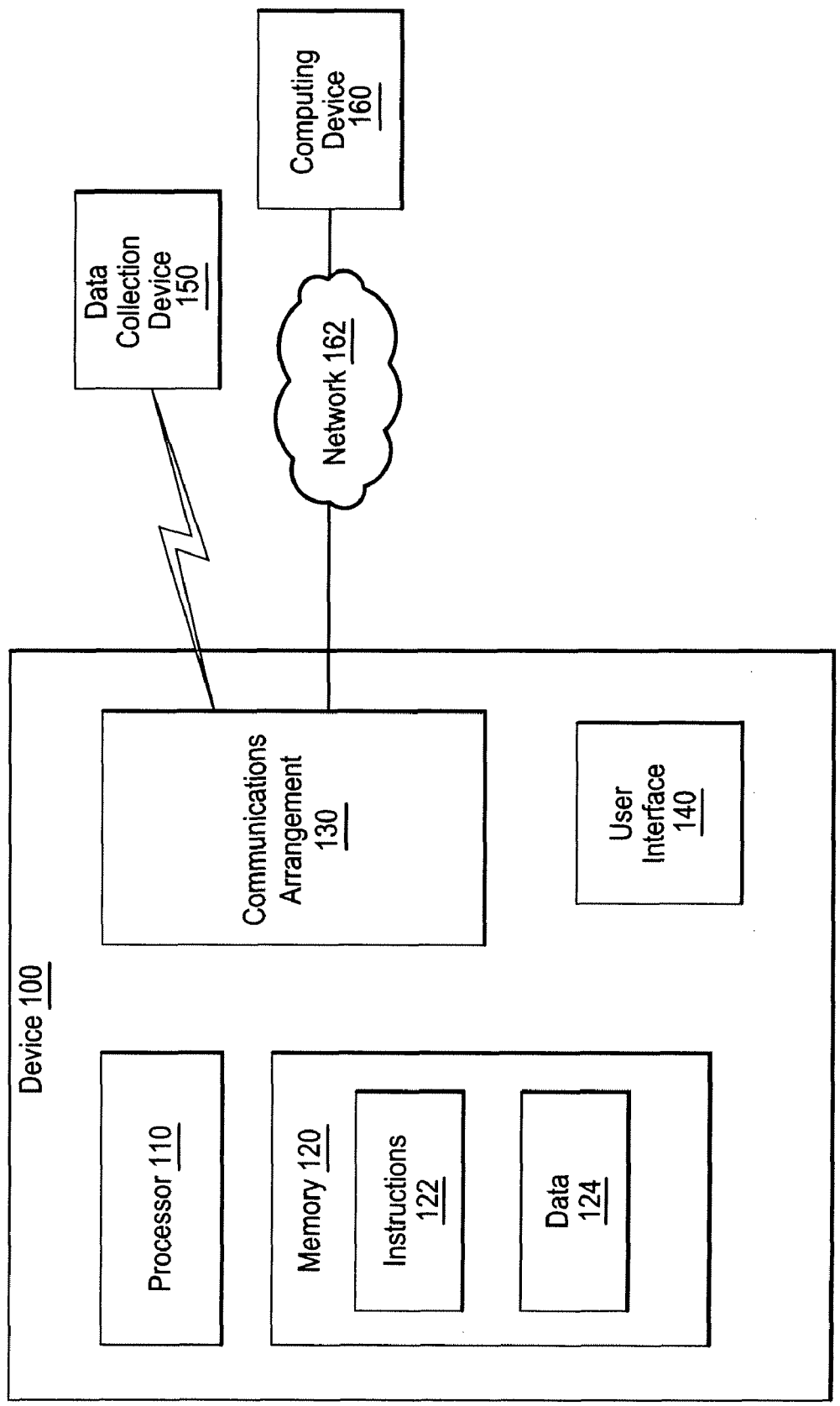
FIG. 9 shows an example of a system for eliminating baseline drift from or at least reducing baseline drift in a bio signal according to an example embodiment of the present invention.

FIG. 9 shows an example of a system for eliminating baseline drift from or at least reducing baseline drift in a bio signal according to an example embodiment of the present invention. The system may include a device 100, which may include a processor 110, a memory 120, a communications arrangement 130 and a user interface 140. The device 100 may be configured to perform the method 300 previously described. In particular, the processor 110 may be configured to execute instructions 122 located in the memory 120. The instructions 122 may include instructions for performing the fitting of the baseline function and the subtracting of the baseline function from the digital signal to produce the flat-baselined signal. The processor may include a microprocessor, an integrated circuit or series of integrated circuits, analog, digital, and other hardware components.

The memory may be a computer-readable storage medium that includes any type of readable or writable memory, including RAM, ROM, flash memory, an optical or electromagnetic drive, a compact disc, etc. In addition to storing the instructions 122, the memory may also include data 124 used in performing the method 300. For example, the data 124 may include digital values, e.g., x-y coordinates, corresponding to the digital signal. The data 124 may also include the cutoff frequency, the range of frequency values, the baseline function and the flat-baselined signal.

The communications arrangement 130 may include any combination of hardware or software components for communicating with a data source such as a data collection device 150 or a computing device 160. The data source may be configured to collect the digital signal and transmit it to the device 100 via the communications arrangement 130. The communications arrangement 130 may be in wired and/or wireless communication with the data source. For example, the communications arrangement 130 may wirelessly communicate with the device 150. The communications arrangement 130 may also be in wired communication with the device 160 via a network 162, which may be a local area network, a wide area network, a telephone network, the Internet, etc.

Data may be collected and transmitted to the device 100 in substantially real time. For example, the device 150 may include sensor electrodes for generating EKG signals. An analog EKG signal may be processed and converted to a digital signal, then transmitted. Data collection may also be done any time after the analog signal is recorded. For example, analog or digital signals may be stored in a database on the device 160, batch processed, and transmitted together. The device 160 may, similar to the device 150, include sensors for measuring EKG signals. Alternatively, the device 160 may be configured to communicate with an external sensing device. In further embodiments, data may be transmitted to the device 160 via manual input, a storage device such as a CD-ROM, or any other input arrangement.

It will be appreciated that the example systems, devices and methods described above may be integrated into a system for monitoring patient health. An example of a system which may be suitable for use with the present invention is described in U.S. patent application Ser. No. 11/938,409, Method and System for Active Patient Management, which describes an active patient management system for monitoring patient EKG signals along with other health indicators. In one embodiment, the method 300 may be implemented in the active patient management system as a software program stored in a computer readable medium such as hard drive memory, flash memory, floppy disk memory, optically-encoded memory (e.g., a compact disk, DVD-ROM, DVD±R, CD-ROM, CD±R, holographic disk), a thermomechanical memory (e.g., scanning-probe-based data-storage), or any type of machine-readable (e.g., computer-readable) storage medium.

The example systems and methods of the present invention described above have been shown to reduce or eliminate low frequency baseline drift in EKG signals. It will be appreciated that the systems and methods of the present invention may also be used to reduce or eliminate high frequency noise in any type of digital signal. In another embodiment, high frequency cutoff values may be used to remove high frequency noise in EKG signals. In this manner, both high and low frequency noise may be reduced or eliminated.

In the preceding specification, the present invention has been described with reference to specific example embodiments thereof. It will, however, be evident that various modifications and changes may be made thereunto without departing from the broader spirit and scope of the present invention as set forth in the claims that follow. The specification and drawings are accordingly to be regarded in an illustrative rather than restrictive sense.

The invention claimed is:

1. A computer-based method for reducing baseline drift in a biological (bio) signal, the method comprising:
    dividing the bio signal into a plurality of shorter signals having fixed time intervals;
    fitting a corresponding portion of a baseline function to a baseline of a respective one of each of the shorter signals;
    subtracting the baseline function from the bio signal, thereby flattening the baseline of the bio signal;
    setting a total number of the time intervals to be equal to a total number of samples of the bio signal contained in a single cycle of a first frequency value associated with the baseline drift; and
    repeating the steps of dividing, fitting, subtracting and setting, while substituting a second frequency value associated with the baseline drift for the first frequency value.

2. The method of claim 1, wherein the first frequency value lies in a range from 0.5 Hertz to 150 Hertz.

3. The method of claim 1, wherein the fitting is performed using cubic-spline interpolation.

4. The method of claim 1, wherein the fitting is performed using a least squares fit.

5. The method of claim 1, wherein the second frequency value is of higher value than the first frequency value.

6. The method of claim 1, wherein the steps are repeated based on an evaluation of a flatness of the bio signal after the subtracting is performed.

7. The method of claim 1, wherein the bio signal is an electrocardiogram signal.

8. The method of claim 1, in which baseline drift is eliminated resulting in a flat baseline of the bio signal.

9. The method of claim 1, wherein the first and the second frequency values are selected from a frequency range in which, independent of the bio signal and how the bio signal is sampled, the baseline drift is expected to occur.

10. A computer-based method for reducing baseline drift in a biological (bio) signal, the method comprising:
    dividing the bio signal into a plurality of shorter signals having fixed time intervals;
    fitting a baseline function to a baseline of each of the shorter signals;
    subtracting the baseline function from the bio signal, thereby flattening the baseline of the bio signal;
    setting a total number of the time intervals to be equal to a total number of samples of the bio signal contained in a single cycle of a first frequency value associated with the baseline drift;
    repeating the steps of dividing, fitting, subtracting and setting, while substituting a second frequency value associated with the baseline drift for the first frequency value, wherein the steps are repeated based on an evaluation of a flatness of the bio signal after the subtracting is performed; and
    evaluating the flatness by fitting an evaluation function to the bio signal and examining a magnitude of the evaluation function.

11. The method of claim 10, further comprising:
    repeating the steps when the magnitude exceeds a predetermined threshold value.

12. A computer-based method for reducing baseline drift in a biological (bio) signal, the method comprising:
    dividing the bio signal into a plurality of shorter signals having fixed time intervals;
    fitting a baseline function to a baseline of each of the shorter signals;
    subtracting the baseline function from the bio signal, thereby flattening the baseline of the bio signal;
    setting a total number of the time intervals to be equal to a total number of samples of the bio signal contained in a single cycle of a first frequency value associated with the baseline drift; and
    repeating the steps of dividing, fitting, subtracting and setting, while substituting a second frequency value associated with the baseline drift for the first frequency value, wherein the steps are repeated as a function of a comparison between a variation in a value of the baseline function to a resolution of an analog-to-digital converter used to generate the bio signal.

13. The method of claim 12, further comprising:
    repeating the steps when the variation exceeds the resolution.

14. A device for reducing baseline drift in a biological (bio) signal, the device being constructed and arranged to:

divide the bio signal into a plurality of shorter signals having fixed time intervals;

fit a corresponding portion of a baseline function to a baseline of a respective one of each of the shorter signals;

subtract the baseline function from the bio signal, thereby flattening the baseline of the bio signal; and set a total number of the time intervals to be equal to a total number of samples of the bio signal contained in a single cycle of a first frequency value associated with the baseline drift, the device comprising:

a communications arrangement configured to receive the bio signal; and a processor configured to divide the bio signal into a plurality of shorter signals having fixed time intervals, fit the corresponding portion of the baseline function to the baseline of the respective one of each of the shorter signals, subtract the baseline function from the bio signal, thereby flattening the baseline of the bio signal, and set the total number of the time intervals to be equal to the total number of samples of the bio signal contained in the single cycle of the first frequency value associated with the baseline drift; and a memory including instructions configuring the processor to divide the bio signal into the plurality of shorter signals having fixed time intervals, fit the corresponding portion of the baseline function to the baseline of the respective one of each of the shorter signals, subtract the baseline function from the bio signal, thereby flattening the baseline of the bio signal, and set the total number of the time intervals to be equal to the total number of samples of the bio signal contained in the single cycle of the first frequency value associated with the baseline drift, wherein the instructions direct the processor to:
repeat the steps of dividing, fitting, subtracting and setting, while substituting a second frequency value associated with the baseline drift for the first frequency value.

15. The device of claim 14, wherein the first frequency value lies in a range from 0.5 Hertz to 150 Hertz.

16. The device of claim 14, wherein the processor is configured to perform the fitting using cubic-spline interpolation.

17. The device of claim 14, wherein the processor is configured to perform the fitting using a least squares fit.

18. The device of claim 14, wherein the second frequency value is of higher value than the first frequency value.

19. The device of claim 14, wherein the processor is configured to repeat the steps based on an evaluation of a flatness of the bio signal after performing the subtracting.

20. The device of claim 14, wherein the bio signal is an electrocardiogram signal.

21. The device of claim 14, wherein the first and the second frequency values are selected from a frequency range in which, independent of the bio signal and how the bio signal is sampled, the baseline drift is expected to occur.

22. A device for reducing baseline drift in a biological (bio) signal, the device being constructed and arranged to:

divide the bio signal into a plurality of shorter signals having fixed time intervals;

fit a baseline function to a baseline of each of the shorter signals;

subtract the baseline function from the bio signal, thereby flattening the baseline of the bio signal; and set a total number of the time intervals to be equal to a total number of samples of the bio signal contained in a single cycle of a first frequency value associated with the baseline drift, the device comprising:

a communications arrangement configured to receive the bio signal;

a processor configured to divide the bio signal into the plurality of shorter signals having fixed time intervals, fit the baseline function to the baseline of each of the shorter signals, subtract the baseline function from the bio signal, thereby flattening the baseline of the bio signal, and set the total number of the time intervals to be equal to the total number of samples of the bio signal contained in the single cycle of the first frequency value associated with the baseline drift; and a memory including instructions configuring the processor to divide the bio signal into the plurality of shorter signals having fixed time intervals, fit the baseline function to the baseline of each of the shorter signals, subtract the baseline function from the bio signal, thereby flattening the baseline of the bio signal, and set the total number of the time intervals to be equal to the total number of samples of the bio signal contained in the single cycle of the first frequency value associated with the baseline drift, wherein the processor is configured to:
repeat the steps of dividing, fitting, subtracting and setting, while substituting a second frequency value associated with the baseline drift for the first frequency value, wherein the steps are repeated based on an evaluation of a flatness of the bio signal after performing the subtracting, and evaluate the flatness by fitting an evaluation function to the bio signal and examining a magnitude of the evaluation function.

23. The device of claim 22, wherein the processor is configured to repeat the steps when the magnitude exceeds a predetermined threshold value.

24. A device for reducing baseline drift in a biological (bio) signal, the device being constructed and arranged to:

divide the bio signal into a plurality of shorter signals having fixed time intervals;

fit a baseline function to a baseline of each of the shorter signals;

subtract the baseline function from the bio signal, thereby flattening the baseline of the bio signal; and set a total number of the time intervals to be equal to a total number of samples of the bio signal contained in a single cycle of a first frequency value associated with the baseline drift, the device comprising:

a communications arrangement configured to receive the bio signal;

a processor configured to divide the bio signal into the plurality of shorter signals having fixed time intervals, fit the baseline function to the baseline of each of the shorter signals, subtract the baseline function from the bio signal, thereby flattening the baseline of the bio signal, and set the total number of the time intervals to be equal to the total number of samples of the bio signal contained in the single cycle of the first frequency value associated with the baseline drift; and a memory including instructions configuring the processor to divide the bio signal into the plurality of shorter signals having fixed time intervals, fit the baseline function to the baseline of each of the shorter signals, subtract the baseline function from the bio signal, thereby flattening the baseline of the bio signal, and set the total number of the time intervals to be equal to the total number of samples of the bio signal contained in the single cycle of the first frequency value associated with the baseline drift, wherein the processor is configured to repeat the steps of dividing, fitting, subtracting and setting, while substituting a second frequency value associated with the baseline drift for the first frequency value, and wherein the steps are repeated as a function of a comparison between a variation in a value of the baseline function to a resolution of an analog-to-digital converter used to generate the bio signal.

25. The device of claim 24, wherein the processor is configured to repeat the steps when the variation exceeds the resolution.

26. A computer-readable storage medium having stored thereon a series of instructions executable by a processor for removing noise from a digital signal, the instructions configured to cause the processor to perform the steps of:

dividing the bio signal into a plurality of shorter signals having fixed time intervals;

fitting a corresponding portion of a baseline function to a baseline of a respective one of each of the shorter signals;

subtracting the baseline function from the bio signal, thereby flattening the baseline of the bio signal;

setting a total number of the time intervals to be equal to a total number of samples of the bio signal contained in a single cycle of a first frequency value associated with the baseline drift; and repeating the steps of dividing, fitting, subtracting and setting, while substituting a second frequency value associated with the baseline drift for the first frequency value.

27. The computer-readable storage medium of claim 26, wherein the first and the second frequency values are selected from a frequency range in which, independent of the bio signal and how the bio signal is sampled, the baseline drift is expected to occur.

* * * * *